| United States Patent [19] | [11] Patent Number: 4,933,166 |
|---|---|
| Shen et al. | [45] Date of Patent: Jun. 12, 1990 |

[54] METHOD OF SAFENING FUNGICIDAL COMPOSITIONS

[75] Inventors: Sue C. Y. Shen, Dallas; William G. Hairston, Garland, both of Tex.

[73] Assignee: American Cyanamid Company, Stamford, Conn.

[21] Appl. No.: 108,239

[22] Filed: Oct. 13, 1987

[51] Int. Cl.$^5$ .................. A61K 7/047; A61K 7/08; A61K 7/15; A61K 7/46
[52] U.S. Cl. .......................................... 424/10; 71/96; 514/127; 514/231.2; 514/255; 514/352; 514/385; 514/399; 514/400
[58] Field of Search ................ 71/96; 514/127, 231.2, 514/255, 352, 383, 399, 400; 424/10

[56] References Cited

U.S. PATENT DOCUMENTS

| 2,596,076 | 5/1952 | Hook et al. | 514/127 |
|---|---|---|---|
| 2,970,080 | 1/1961 | Oros et al. | 514/127 |
| 3,940,419 | 2/1976 | Diehl et al. | 71/96 |
| 4,017,299 | 4/1977 | Diehl et al. | 71/96 |
| 4,021,228 | 5/1977 | Arneklov et al. | 71/96 |
| 4,433,997 | 2/1984 | Pallos | 71/95 |
| 4,488,898 | 12/1984 | Fory et al. | 71/96 |
| 4,695,564 | 9/1987 | Walgenbach | 514/127 |

*Primary Examiner*—Ferris H. Lander
*Attorney, Agent, or Firm*—John W. Hogan, Jr.

[57] ABSTRACT

The present invention relates to methods for safening seeds and crop plants from the undesirable effects often encountered when treating said seeds and crop plants with ergosterol biosynthesis inhibiting fungicides. The method involves treating said seed and/or crop plant with the disclosed phthalimide compounds.

13 Claims, No Drawings

METHOD OF SAFENING FUNGICIDAL COMPOSITIONS

BACKGROUND OF THE INVENTION

The present invention relates to methods for safening seeds and/or crop plants treated with sterol inhibiting fungicides, ergosterol biosynthesis inhibiting fungicides.

The discovery and development of fungicides which inhibit fungal ergosterol biosynthesis (sterol inhibiting or SI activity) has led to the introduction of compounds which possess a broad spectrum of fungicidal activity and are particularly effective in controlling powdery mildews, rusts, scab, leafspots and the like in a variety of crops. These compounds, most of which also exhibit systemic fungicidal activity, are in general heterocyclic compounds containing one or more heteroatoms in at least one ring. A review article by T. Kato, in *Japan Pesticide Information* No. 46. (1985), pp 3 –6 identifies twenty-one compounds divided into six heterocyclic groups i.e. pyridines, pyrimidines, imidazoles, triazoles, piperazines and morpholines which exhibit SI activity.

While these fungicides are highly effective for the control of a wide range of fungi, both as foliar sprays and as seed treatments, undesirable phytotoxic effects, such as slowing the rate of emergence and reducing stands of plants when applied as seed treatments have been reported, i.e. P. Phipps, *Plant Disease*, 69 (11): pp. 1009-2020 (1985); H. Buchenauer et al, *Zeitschrift fur Pflanzenkrankheiten und Pflanzenschutz (Journal of Plant Diseases and Protection* 91 (5): 506-524 (1984)).

In other studies, H. Buchenauer, E. Roehner CA94(25):203812e (*Pestic. Biochem. Physoil.*, 15(1), 58-70) reported that the fungicides, triadimefon and triadimenol, markedly reduced growth of coleoptiles, primary leaves and barley seedlings roots when grown for 7 days in petri dishes in the dark. Gibberellins ($A_1$, $A_3$, $A_4A_7$, $A_9$) alleviated growth retardation of primary leaves and coleoptiles induced by the fungicides, whereas fungicide-induced growth retardation of the shoots was partly relieved by kinetin, and IAA did not show any alleviating activity. The fungicides also were found to substantially retard the elongation of shoots of tomato and cotton plants while simultaneous application of gibberellic acid ($GA_3$) nullified the retardation. The fungicides only slightly interfered with both $\alpha$-amylase production of intact germinating barley seed and the $GA_3$-induced $\alpha$-amylase synthesis in barley endosperm. Both compounds also interferred with sterol metabolism of shoots of barley seedlings when compared with control plants; treatment resulted in lower amounts and altered proportions of C-4,4-desmethyl sterols. Based upon these studies, it was assumed that these fungicides interfer with gibberellin and sterol biosynthesis in barley seedlings, thereby providing for interfering in the seed's and/or crop plant's development as well. Thus, while beneficial fungicidal activity was obtained, phytotoxic effects also were apparent.

SUMMARY OF THE INVENTION

The present invention relates to methods for safening seeds and/or crop plants when treated with fungicides by treating said seeds and/or crop plants with an effective amount of one or more ergosterol biosynthesis inhibiting fungicid compounds and an effective amount of a phthalimide compound represented by the structure:

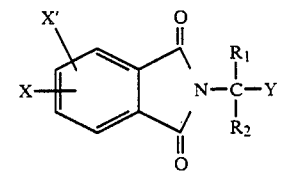

or

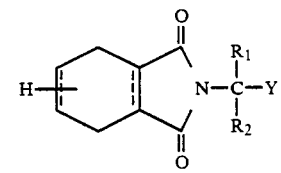

wherein W is hydrogen or alkyl $C_1$–$C_4$; X and X' each represent hydrogen, halogen, alkyl $C_1$–$C_4$, $CF_3$, alkoxy ($C_1$–$C_4$), benzyloxy, di($C_1$–$C_4$)alkylamino, $C_1$–$C_4$ alkylthio, hydroxy, $C_1$–$C_4$ alkylsulfonyl, alkanoylamino $C_1$–$C_4$ or nitro; Y is —$COOR_3$, —$CONHR_8$, $CONR_3R_4$, —$CONHN(R_5)_2$, —$CONHN^+(R_6)_3$ ) halide—, —CN or $COR_7$ with the proviso that at least one of X and X' is a substituent other than hydrogen; $R_1$ and $R_2$ each represents alkyl $C_1$–$C_4$ or when taken together with the carbon to which they are attached form cycloalkyl $C_4$–$C_{11}$ optionally substituted with methyl $R_3$ and $R_4$ each represent hydrogen or alkyl $C_1$–$C_4$; $R_5$ and $R_6$ each represent alkyl; $C_1$–$C_2$; $R_7$ is halogen and $R_8$ is —$CH_3$ or

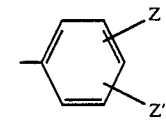

where Z and Z' are hydrogen, halogen, alkyl $C_1$–$C_2$, -$CF_3$ or —$OCH_3$, ═══ is a single or double bond with the proviso that there be only 0 or 1 double bond or isomeric mixtures thereof and mixtures thereof.

It is an object of the present invention to provide safened fungicidal compositions comprised of ergosterol biosynthesis inhibiting fungicides and phthalimide compounds (and diluents and/or carrier thereof) and using said compositions as seed treatments.

It is another object of this invention to provide a method for reducing phytotoxicity of ergosterol biosynthesis inhibiting fungicides utilizing phthalimide compounds. These and other objects of the invention will become apparent by the more detailed description of the invention provided hereinbelow.

DETAILED DESCRIPTION OF THE INVENTION

The present invention relates to methods for safening seeds and/or crop plants when treated with fungiciees by treating said seeds and/or crop plants an effective amount of one or more ergosterol biosynthesis inhibiting fungicide compounds and an effective amount of a phthalimide compound represented by the structure:

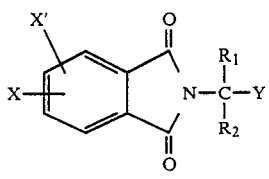

or

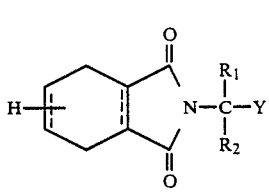

wherein W is hydrogen or alkyl $C_1$-$C_4$; X and X' each represent hydrogen, halogen, alkyl $C_1$-$C_4$, $CF_3$, alkoxy ($C_1$-$C_4$), benzyloxy, di($C_1$-$C_4$)alkylamino, $C_1$-$C_4$ alkylthio, hydroxy, $C_1$-$C_4$ alkylsulfonyl, alkanoylamino $C_1$-$C_4$ or nitro; Y is —$COOR_3$, —$CONHR_8$, —$CONR_3R_4$, —$CONHN(R_5)_2$, —$CONHN^+(R_6)_3$ halide—, —CN or $COR_7$ with the proviso that at least one of X and X' is a substituent other than hydrogen; $R_1$ and $R_2$ each represent alkyl $C_1$-$C_4$ or when taken together with the carbon to which they are attached form cycloalkyl $C_4$-$C_{11}$ optionally substituted with methyl $R_3$ and $R_4$ each represent hydrogen or alkyl $C_1$-$C_4$; $R_5$ and $R_6$ each represent alkyl $C$-$C_2$; $R_7$ is halogen and $R_8$ is —$CH_3$ or

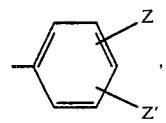

where Z and Z' are hydrogen, halogen, alkyl $C_1$-$C_2$, -$CF_3$ or —$OCH_3$, ══ is a single or double with the proviso that there be only 0 or 1 double bond or isomeric mixtures thereof and mixtures thereof.

The above phthalimide compounds and methods for preparation are described in U.S. Pat. No. 3,940,419, incorporated herein by reference thereto. These phthalimide compounds and their use as plant growth regulating compounds also are described in U.S. Pat. No. 4,017,299, also incorporated herein by reference thereto. Surprisingly, it has been found that treatment of seeds with ergosterol biosynthesis inhibiting fungicides and the disclosed phthalimide compounds results in safening from the phytotoxic effects encountered by treatment with the fungicide alone. Treatment of small grain seeds, such as wheat and barley, with both a fungicidally-effective amount of ergosterol biosynthesis inhibiting fungicides and phthalimide compound(s) at rates of 50 ppm to 2000 ppm results in both significantly improved early seedling vigor and improved stand establishment of grains when compared to seed treated with the fungicide alone.

Ergosterol biosynthesis inhibiting fungicides preferred for treatments and compositions of this invention include the pyridine, pyrimidine, imidazole, triazole, piperazine, and morpholine compounds listed in Table I, and mixtures thereof:

TABLE I[1]

Fungicides Inhibiting Ergosterol Biosynthesis

| Chemical group | Common name | Chemical structure |
|---|---|---|
| Pyridines | buthiobate | ![pyridine-N=C(S-n.Bu)SCH2-C6H4-t.Bu] |
| Pyrimidines | triarimol | ![triarimol structure with 2,4-dichlorophenyl, phenyl, OH, pyrimidinyl] |
| | fenarimol | ![fenarimol structure with 2-chlorophenyl, 4-chlorophenyl, OH, pyrimidinyl] |

TABLE I-continued

Fungicides Inhibiting Ergosterol Biosynthesis

| Chemical group | Common name | Chemical structure |
|---|---|---|
| | nuarimol | (structure) |
| Imidazoles | imazalil | (structure) |
| | prochloraz | (structure) |
| | triflumizole | (structure) |
| Triazoles | triadimefon | (structure) |
| | triadimenol | (structure) |
| | bitertanol | (structure) |
| | fluotrimazole | (structure) |

TABLE I-continued

Fungicides Inhibiting Ergosterol Biosynthesis

| Chemical group | Common name | Chemical structure |
|---|---|---|
| Triazoles | etaconazole | (triazole-N-CH(CH₃)- linked to 1,3-dioxolane bearing 2,4-dichlorophenyl and Et substituent) |
| | propiconazole | (triazole-N-CH(CH₃)- linked to 1,3-dioxolane bearing 2,4-dichlorophenyl and n.Pr substituent) |
| | penconazole | (triazole-N-CH₂CH(n.Pr)-2,4-dichlorophenyl) |
| | diclobutrazol | (triazole-N-CH(CH₂-2,4-dichlorophenyl)-CH(OH)-t.Bu) |
| | flutriafen | (triazole-N-CH₂-C(OH)(4-fluorophenyl)(2-fluorophenyl)) |
| Triazoles | code No. S-33081 | (triazole-N-C(=CH-2,4-dichlorophenyl)-CH(OH)-t.Bu) |
| | code No. DPX 116573 | (triazole-N-CH₂-Si(CH₃)(4-fluorophenyl)(4-fluorophenyl)) |
| Piperazines | triforine | Cl₃CCHNHCHO–N(piperazine)N–CHNHCHCCl₃ (both N substituents: Cl₃CCHNHCHO) |

TABLE I[1]-continued

Fungicides Inhibiting Ergosterol Biosynthesis

| Chemical group | Common name | Chemical structure |
| --- | --- | --- |
| Morpholines | tridemorph | (morpholine ring with two CH$_3$ groups and N—C$_{13}$H$_{27}$) |
|  | fenpropimorph | (morpholine ring with two CH$_3$ groups, N—CH$_2$CHCH$_2$— with CH$_2$ branch —phenyl—t.Bu) |

[1] T. Kato, Japan Pesticide Information NO46 (1985)

A more preferred group of said fungicide compounds for use in the treatments and compositions of this invention include imazalil, triadimefon and triadimenol.

A most preferred embodiment of this invention is the use of triadimenol alone or in combination with another fungicide in conjunction with a phthalimide compound as described herein.

Preferred phthalimides for use in the treatments and compositions of this invention are those wherein Y is CONR$_3$R$_4$, CONHN(R$_5$)$_2$, CONHN$^{30}$ (R$_6$)$_3$. halide, CN, COR$_7$ or CONHR$_8$.

A more preferred group of phthalimides compounds are those wherein Y is CONR$_3$R$_4$.

A most preferred group of phthalimide compounds includes:
1-(3-chlorophthalimido)cyclohexanecarboxamide,
1-(3-chlorophthalimido)cyclopentanecarboxamide,
1-(4-chlorophthalimido)cyclohexanecarboxamide,
1-(4-methylphthalimido)-1-cyclohexanecarboxamide,
1-(3,4,5,6-tetrahydrophthalimido)-1-cyclohexanecarboxamide,
α-isobutyl-α,ethyl-α-(3-chlorophthalamido)acetamide,
1-(3-trifluoromethylphthalimido) cyclohexanecarboxamide or 1-(3,5-dichlorophthalamido)--cyclohexanecarboxamide In preferred embodiments of this invention the 1(3-chlorophthalimido) cyclohexanecarboxamide is used in conjunction with the fungicides listed in Table I. Combinations and treatments which employ imazalil, triadimefon, triadimenol or a mixture thereof, are preferred and treatments and compositions with triadimenol alone or in combination with another fungicide compound are most preferred.

In accordance with the seed treatment method of this invention the active fungicide and phthalimide compound may be applied individually or as a combination composition to seed in dry or wet form. Dry treatments consist of the active compound(s) in an inert dust (carrier) that may contain additives to prevent cohesion into lumps or stickers to improve adhesion to the seed. Wetting agent(s) may be added so that the powder can be wetted with water and used as a slurry treatment. Wet treatments can be applied by steeping the seed in a solution of active compound(s) in water or other solvents or by a slurry method often with a surfactant(s).

Low volume liquid treatments are sometimes used, in which the active compound(s) is applied at a high concentration in a suitable solvent. Such treatments avoid the problems of having to dry the seed or sowing immediately after treatment to prevent premature germination. Quick-drying emulsion treatments which allows application of very large doses may also be employed.

Wettable powders of the individual compounds or a combination of the compounds can be prepared by blending with a solid carrier, such as attapulgite, kaolin, diatomaceous earth, silica, or the like, and a small amount of a dispersant and wetting agent and air-milling the blended mixture to effect reduction of particle size to about the 5 micron to 10 micron range. A typical wettable powder might contain 50.0% by weight of the active compound(s), 5.0% by weight of a highly purified partially desulfonated sodium lignin sulfonate 1.0% by weight of sodium N-methyl-N-oleoyltaurate and 44.0% by weight of attapulgite.

In practice, it is found that the active compound in the above formulation varies from about 10.0% to 80.0% by weight. However, in such cases, the solid diluent is varied accordingly.

For the preparation of a dust, for example a 10% dust, 20% by weight of the 50% wettable powder is blended with about 80% by weight of a solid carrier, such as kaolin. Suitable equipment for such preparations are ribbon-type blenders and double-cone blenders. It is also obvious that the concentration of active compound(s) in dust formulations are varied by adjusting the amount of wettable powder and carrier used. Typical dusts will generally vary between about 0.5% to 15.0% by weight of active compound(s), although higher concentrations may also be prepared.

An alternative process for preparation of dusts, also dust concentrates, involves blending the active compound(s) with the solid carrier and passing the uniform blend through an attrition mill to obtain the desired particle size.

Other formulations, methods, products and advantages of the present invention may become apparent from the examples set forth hereinbelow. These examples are provided simply as an illustration of the invention and are not intended to be limiting thereon.

EXAMPLE 1-3

Efficacy and safening of seed treatments of the invention

Seeds of three varieties of winter wheat:
(1) Hybrex HW 1030 - a hydrid single gene semi-dwarf (2) McNair 1003 - a non-semi-dwarf
(3) Coker 916 - a standard single gene semi-dwarf are treated with the ergosterol biosynthesis inhibiting fungicide, tridimenol, at a rate of 1.5 fl. oz./cwt. and 3 rates of the phthalimide compound 1-(3-chlorophthalimido)cyclohexanecarboxamide: 3.2 fl. oz/cwt (1000ppm), 1.6 fl oz./cwt (500ppm) and 0.32 fl. oz/cwt (100ppm). The seeds are then sown in rows in the field by standard practices. Four weeks after planting the resulting plants are rated for plant vigor on a scale of 1 to 10, with higher numbers indicating superior plant vigor. The number of plants per row are counted at five weeks after planting. The results of these examples summarized in Table II demonstrate the safenening effect by improved plant vigor and stand obtained by the treatment of seeds with triadimenol and the phthalimide compound 1-(3-chlorophthalimido)cyclohexanecarboxamide compared to the treatment with the fungicide alone.

TABLE II

| | Example 1 | | Example 2 | | Example 3 | | | |
|---|---|---|---|---|---|---|---|---|
| | Variety: | | | | | | | |
| | Hybrex HW 1030 | | McNair 1003 | | Coker 916 | | Average | |
| Treatment | Stand Plts/Row | Vigor 1–10 | Stand Plts/Row | Vigor 1–10 | Stand Plts/Row | Vigor 1–10 | Stand Plts/Row | Vigor 1–10 |
| Water (control) | 258.0 | 6.25 | 200 | 6.25 | 246.0 | 7.25 | 234.7 | 6.58 |
| triadimenol @ 1.5 fl. oz./cwt. | 206.3 | 4.5 | 179 | 4.75 | 246.0 | 6.25 | 210.4 | 5.25 |
| triadimenol @ 1.5 1-(3-chlorophtha-limdo)cyclohexane-carboxamide, @ 3.2 oz./cwt | 260.5 | 8.5 | 190.5 | 8.50 | 237.0 | 10.0 | 229.3 | 9.00 |
| triadimenol @ 1.5 1-(3-chlorophtha-limido)cyclohexane-carboxamide, @ 1.6 oz./cwt | 258.7 | 8.0 | 181.0 | 8.25 | 239.7 | 9.0 | 226.5 | 8.42 |
| triadimenol @ 1.5 1-(3-chlorophtha-limido)cyclohexane-carboxamide, @ 0.32 oz./cwt | 268.2 | 7.0 | 217.7 | 7.25 | 251.5 | 8.25 | 245.8 | 7.50 |

What is claimed is:

1. A method for safening seeds treated with one or more ergosterol biosynthesis inhibiting fungicide(s), said method comprising: treating said seeds with an effective amount of a phthalimide compound represented by the structure,

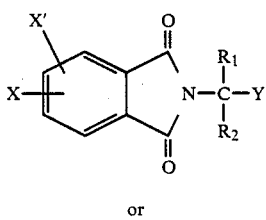

or

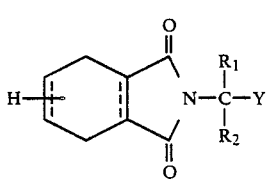

wherein W is hydrogen or alkyl $C_1$–$C_4$; X and X' each represent hydrogen, halogen, alkyl $C_1$–$C_4$, $CF_3$, alkoxy ($C_1$–$C_4$), benzyloxy, di($C_1$–$C_4$)alkylamino, $C_1$–$C_4$ alkylthio, hydroxy, $C_1$–$C_4$ alkylsulfonyl, alkanoylamino $C_1$–$C_4$ or nitro; Y is —$COOR_3$, —$CONHR_8$, —$CONR_3R_4$, —$CONHN(R_5)_2$, —$CONHN^+(R_6)_3$ halide—, —CN or $COR_7$ with the proviso that at least one of X and X' is a substituent other than hydrogen; $R_1$ and $R_2$ each represent alkyl $C_1$–$C_4$ or when taken together with the carbon to which they are attached form cycloalkyl $C_4$–$C_{11}$ optionally substituted with methyl $R_3$ and $R_4$ each represent hydrogen or alkyl C–$C_4$; $R_5$ and $R_6$ each represent alkyl $C_1$–$C_2$; $R_7$ is halogen and $R_8$ is —$CH_3$ or

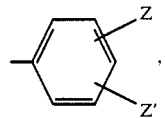

where Z and Z' are hydrogen, halogen, alkyl $C_1$–$C_2$, $CF_3$ or —$OCH_3$, ===== is a single or double bond with the proviso that there be only 0 or 1 double bond or isomeric mixtures thereof and mixtures thereof and treating said seed with an ergosterol biosynthesis inhibiting fungicide.

2. The method according to claim 1, wherein said fungicide is imazalil, triadimefon, triadimenol or mixtures thereof.

3. The method according to claim 2, wherein said phthalimide is Y is $CONR_3R_4$.

4. The method according to claim 3, wherein said phthalimide is 1-(3-chlorophthalimido)cyclohexanecarboxamide, 1-(3-chlorophthalimido)cyclopentanecarboxamide, (4-chlorophthalimido)cyclohexanecarboxamide, 1-(4-methylphthalimido)-1-cyclohexanecarboxamide,1-(3, 4,5,6-tetrahydrophthalimido)-1-cyclohexanecarboxamide, αisobutyl-α-methyl-α-(3-chlorophthalamido)acetamide, 1-(3-trifluoromethylphthalimido)cyclohexanecarboxamide or 1-(3,5-dichlorophthalamido)-1-cyclohexancarboxamide.

5. The method according to claim 4, wherein said fungicide is triadimenol.

6. The method according to claim 5, wherein said phthalimide compound is 1-(3-chlorophthalimido) cyclohexanecarboxamide.

7. Safened fungicidal compositions for the treatment of seeds, said compositions comprising: an effective amount of one or more ergosterol biosynthesis inhibiting fungicide compounds and an effective amount of a phthalimide compound represented by the structure;

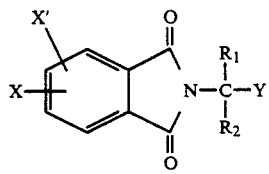

or

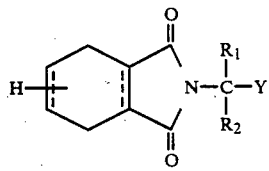

wherein W is hydrogen or alkyl $C_1$-$C_4$; X and X' each represent hydrogen, halogen, alkyl $C_1$-$C_4$, $CF_3$, alkoxy ($C_1$-$C_4$), benzyloxy, di($C_1$-$C_4$) alkylamino, $C_1$-$C_4$ alkylthio, hydroxy, $C_1$-$C_4$ alkylsulfonyl, alkanoylamino $C_1$-$C_4$ or nitro; Y is —$COOR_3$, —CONHR$_8$, —$CONR_3R_4$, —$CONHN_{(6)2}$, —$CONHN^+(R_6)_3$ halide—, —CN or $COR_7$ with the proviso that at least one of X and X' is a substituent other than hydrogen; $R_1$ and $R_2$ each represent alkyl $C_1$-$C_4$ or when taken together with the carbon to which they are attached form cycloalkyl $C_4$-$C_{11}$ optionally substituted with methyl $R_3$ and $R_4$ each represent hydrogen or alkyl $C_1$-$C_4$; $R_5$ and $R_6$ each represent alkyl $C_1$-$C_2$; $R_7$ is halogen and $R_8$ is —$CH_3$ or

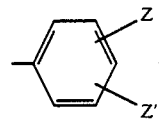

where Z and Z' are hydrogen, halogen, alkyl $C_1$-$C_2$, —$CF_3$ or —$OCH_3$, ===== is a single or double bond with the proviso that there be only 0 or 1 double bond or isomeric mixtures thereof and mixtures thereof, a fungicide; and carrier or diluent thereof.

8. The composition according to claim 7, wherein said fungicide is imazalil, triadimefon, triadimenol or mixtures thereof.

9. The method according to claim 8, wherein said phthalimide compound is wherein Y is $CONR_3R_4$.

10. The composition according to claim 7, wherein the phthalimide compound is 1-(3-chlorophthalimido)-cyclohexanecarboxamide, 1-(3-chlorophthalimido) cyclopentanecarboxamide, 1-(4-chlorophthalimido)cyclohexanecarboxamide, -(4-methylphthalimido)-1-cyclohexanecarboxamide, 1-(3,4,5,6-tetrahydrophthalimido)-1-cyclohexanecarboxamide, α-isobutyl-α-methyl-αo-(3-chlorophthalamido) acetamide,1-(3-trifluoromethylphthalimido)cyclohexanecarboxamide or 1-(3,5-dichlorophthalamido)-1cyclohexanecarboxamide.

11. The composition according to claim 10, wherein said fungicide is triadimenol.

12. The composition according to claim 11, wherein said phthalimide compound is 1-(3-chlorophthalimido)-cyclohexanecarboxamide.

13. The method according to claim 1 wherein said effective amount of phthalimide is 50 ppm to 2000 ppm.

* * * * *

UNITED STATES PATENT OFFICE
CERTIFICATE OF CORRECTION

Page 1 of 2

Patent No. 4,933,166           Dated June 12, 1990

Inventor(s) Sue C. Y. Shen et al.

It is certified that error appears in the above-identified patent and that said Letters Patent is hereby corrected as shown below:

Claim 1, Column 12, line 19
...$CF_3$ or $-OCH_3$, ——— is a single or double bond with should read:

...$CF_3$ or $-OCH_3$, ==== is a single or double bond with

Claim 4, Column 12, line 57
boxamide, (4-chlorophthalimido)cyclohexanecarboxashould read:

boxamide, 1-(4-chlorophthalimido)cyclohexanecarboxa-

Claim 7, Column 13, line 30
... Y is $-COOR_3$, -CONHRhd 8, should read:

...Y is $-COOR_3$, $-CONHR_8$

Claim 10, Column 14, line 24
clohexanecarboxamide, -(4-methylphthalimido)-1- should read:

clohexanecarboxamide, 1-(4-methylphthalimido)-1-

Claim 10, Column 14, line 27
methyl-αo-(3-chlorophthalamido) acetamide, 1-(3-trishould read:

methyl-α-(3-chlorophthalamido) acetamide, 1-(3-tri-

Claim 10, Column 14, line 29
1-(3,5-dichlorophthalamido)-1cyclohexanecarboxashould read:

UNITED STATES PATENT AND TRADEMARK OFFICE
CERTIFICATE OF CORRECTION

PATENT NO. : 4,933,166                    Page 2 of 2

DATED     : June 12, 1990

INVENTOR(S) : Sue C. Y. Shen, et. al.

It is certified that error appears in the above-identified patent and that said Letters Patent is hereby corrected as shown below:

1- (3,5-dichlorophthalamido) - 1 -cyclohexanecarboxa-

Signed and Sealed this

Twenty-third Day of February, 1993

Attest:

STEPHEN G. KUNIN

Attesting Officer    Acting Commissioner of Patents and Trademarks